US00PP18193P3

(12) United States Plant Patent
Danziger

(10) Patent No.: US PP18,193 P3
(45) Date of Patent: Nov. 13, 2007

(54) ***JAMESBRITTENIA* PLANT NAMED 'DANBRIT1'**

(50) Latin Name: ***Jamesbrittenia* sp.**
Varietal Denomination: DANBRIT1

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/404,747

(22) Filed: Apr. 17, 2006

(65) Prior Publication Data

US 2007/0245436 P1 Oct. 18, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Foley & Lardner, LLP

(57) ABSTRACT

A new and distinct *Jamesbrittenia* plant named 'DANBRIT1' characterized by having 5-petalled flowers, measuring about 2.0 cm in diameter and dark red in color with a yellow-orange colored throat and center; vigorous growth habit, which maintains a trailing, compact growth habit; early flowering response; and suitable for use with hanging basket planters, combination planters and ground cover under full sunlight and slight shade.

2 Drawing Sheets

Latin name of the genus and species of the claimed plant: *Jamesbrittenia* sp.
Variety denomination: 'DANBRIT1'.

BACKGROUND OF THE INVENTION

The present invention relates to a new and distinct cultivar of *Jamesbrittenia* plant, botanically known as *Jamesbrittenia* sp. of the Scrophulariaceae family, and is hereinafter referred to by the cultivar name 'DANBRIT1'.

The new *Jamesbrittenia* cultivar is a product of a controlled breeding program conducted by the inventor, Gabriel Danziger, in Moshav Mishmar Hashiva, Israel. The objective of the breeding program was to develop a new *Jamesbrittenia* cultivar with large, red flowers and trailing, compact growth habit.

The new *Jamesbrittenia* cultivar originated from a cross made by the inventor, Gabriel Danziger, in 2003 in Moshav Mishmar Hashiva, Israel. The female or seed parent is the *Jamesbrittenia* sp. cultivar designated 'ST-3-120' (unpatented). The male or pollen parent is open pollination. The new *Jamesbrittenia* cultivar was discovered and selected by the inventor, Gabriel Danziger, as a single flowering plant within the progeny of the stated cross in a controlled environment in 2004 in Moshav Mishmar Hashiva, Israel.

Asexual reproduction of the new *Jamesbrittenia* cultivar by vegetative tip cuttings was first peformed in May of 2004 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DANBRIT1', which in combination distinguish this *Jamesbrittenia* as a new and distinct cultivar:

1. 5-petalled flowers, measuring about 2.0 cm in diameter and dark red in color with a yellow-orange colored throat and center;
2. Vigorous growth, which maintains a trailing, compact growth habit;
3. Early flowering response; and
4. Suitable for use with hanging basket planters, combination planters and ground cover under full sunlight and slight shade.

Plants of 'DANBRIT1' differ from the plants of the female parental cultivar in the characteristics described in Table 1:

TABLE 1

| Trait | New Cultivar 'DANBRIT1' | Female Parent 'ST-3-120' |
|---|---|---|
| Flower color | Dark red, Red group RHS 53B | Very dark red, Red group RHS 53A |
| Flower size | Large, about 2.2 cm | Medium, about 1.6 cm |
| Leaf shape | Elliptic, Pinnatifid | Ovate, Pinnatisect |
| Plant height | About 15 cm | About 10 cm |

Of the many commercial cultivars known to the present inventor, the most similar in comparison to the new *Jamesbrittenia* cultivar 'DANBRIT1' is the *Jamesbrittenia* cultivar designated *Jamesbrittenia* 'Centurion Orange' (unpatented) In side-by-side comparisons conducted in Moshav Mishmar Hashiva, Israel, plants of the new *James-*

*brittenia* cultivar 'DANBRIT1' differed from plants of *Jamesbrittenia* 'Centurion Orange' in the characteristics described in Table 2:

TABLE 2

| Trait | New Cultivar 'DANBRIT1' | Comparison Cultivar 'Centurion Orange' |
|---|---|---|
| Flower color | Dark red, Red group RHS 53B | Orange, Orange-Red group RHS 35C |
| Flower size | Large, about 2.2 cm | Medium, about 1.6 cm |
| Leaf shape | Elliptic, Pinnatifid | Ovate, Pinnatisect |
| Plant height | About 15 cm | About 10 cm |

BRIEF DESCRIPTION OF THE DRAWINGS

The accompanying photographs illustrate the overall appearance of the new *Jamesbrittenia* cultivar 'DANBRIT1' showing the colors as true as is reasonably possible with colored reproductions of this type. Colors in the photographs may differ slightly from the color values cited in the detailed botanical description which accurately describe the color of 'DANBRIT1'.

DETAILED BOTANICAL DESCRIPTION

Figure 1:
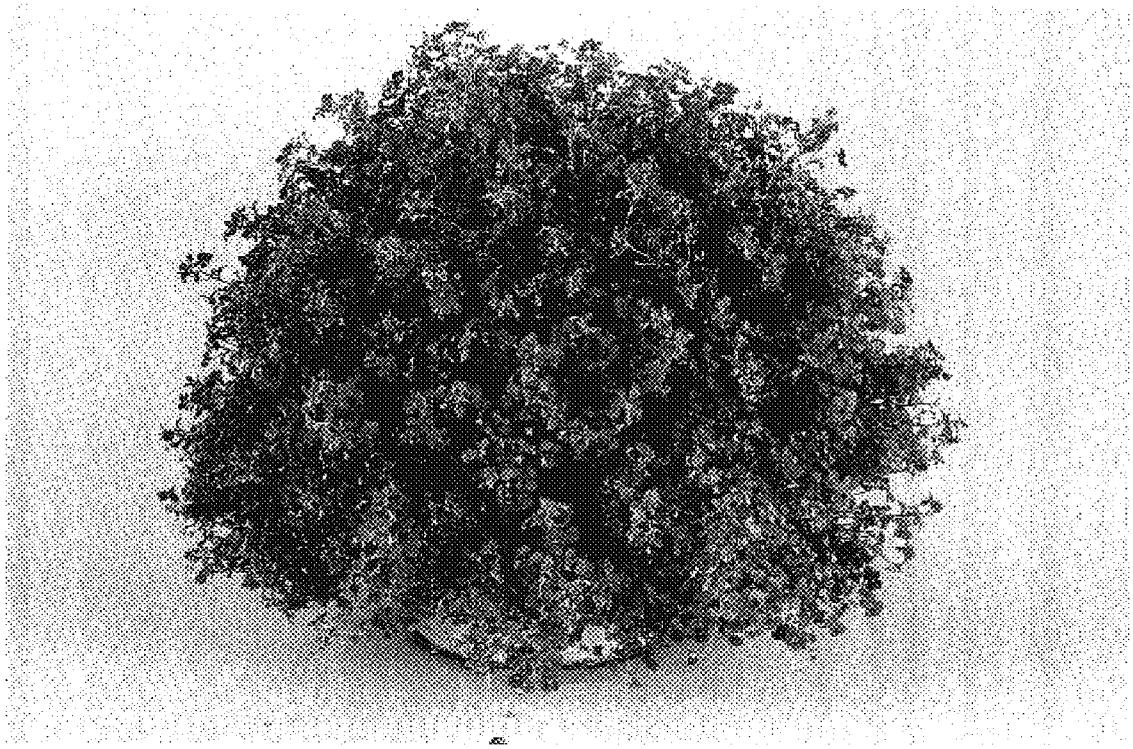
FIG. 1 shows a side view perspective a typical flowering plant of 'DANBRIT1' in a hanging planter, at 3 months of age.
Figure 2:
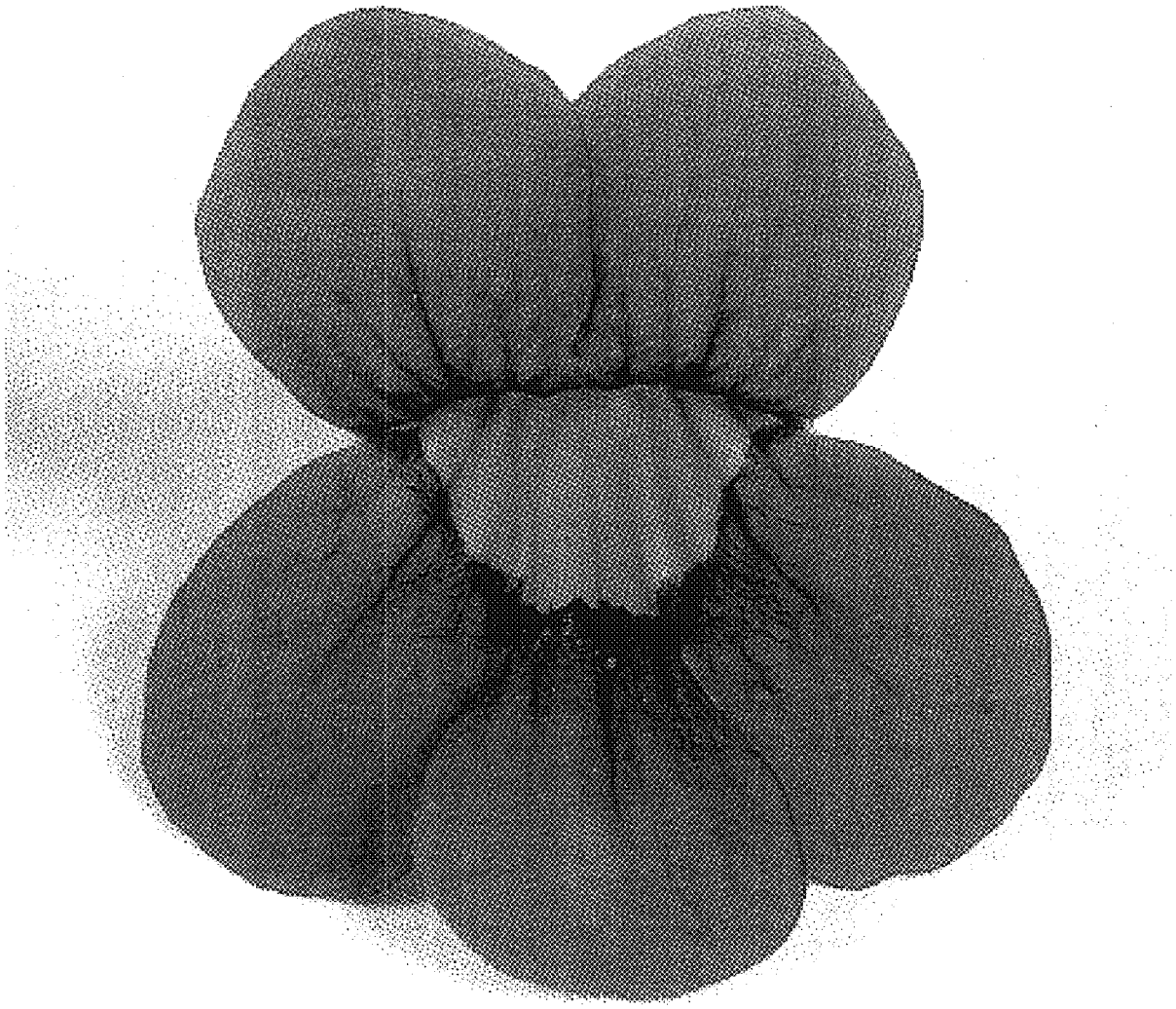
FIG. 2 shows a close-up view of a typical flower of 'DANBRIT1' at 3 months of age.

The new *Jamesbrittenia* cultivar 'DANBRIT1' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Jamesbrittenia* cultivar as grown in a greenhouse in Moshav Mishmar Hashiva, Israel, under conditions which closely approximate those generally used in commercial practice. Greenhouse temperature averages 18° C. at night and 24° C. day. Constant fertilization with a balanced NPK fertilizer at 200 ppm N level and that contains average levels of micronutrients with a slightly increased levels of iron should be used when growing 'DANBRIT1'.

Color references are made to The Royal Horticultural Society Colour Chart (R.H.S.), 2001 edition, except where general colors of ordinary significance are used. Color values were taken under daylight conditions at approximately 12:00 noon in Moshav Mishmar Hashiva, Israel. The age of the plant described is 3 months.

Classification:

*Botanical.*—*Jamesbrittenia* sp.

*Commercial.*—*Jamesbrittenia* Britney™ Maroon.

Parentage:

*Female parent.*—*Jamesbrittenia* sp. cultivar designated 'ST-3-120' (unpatented).

*Male parent.*—Open pollination.

Propagation:

*Type.*—Tip cutting of side shoots.

*Time and temperature to initiate roots.*—About 7 to 10 days at 18° C.

*Time and temperature to produce a rooted cutting.*—About 14 to 18 days at 18° C.

*Rooting habit and description.*—Fine, Fibrous roots.

Growing conditions:

*Light intensities.*—Full sunlight or slight shade.

*Temperature.*—During day: Range of 20° C. to 24° C. During night: Range of 16° C. to 20° C.

*Tolerance.*—Tolerant to a low temperature of about 10° C. and to a high temperature about 30° C.

*Fertilization.*—A balanced fertilizer with level of 200 ppm N level. (please provide, ie. Nitrogen).

*Growth regulators.*—Unnecessary.

Plant:

*General appearance and form.*—Height: About 15 cm. Spread: About 50 cm.

*Shape.*—Rounded and Trailing.

*Vigor.*—Strong.

*Branching habit.*—Vigorously branched.

*Lateral branches.*—

TABLE 3

| Branch Characteristic | Primary | Secondary |
|---|---|---|
| Length | About 45 cm. | About 25 cm. |
| Diameter | About 2 mm. | About 1 mm. |
| Internode Length | About 3 cm. | About 2 cm. |
| Texture | Velvety and sticky | Velvety and sticky |
| Pubescence | Yes | Yes |
| Color | Yellow-Green group, RHS 146B | Yellow-Green group, RHS 146C |

*Crop time.*—About 8 to 10 weeks for a flowering pot.

*Fragrance.*—Lemony. (please provide or state None).

Foliage:

*Overall shape of leaf.*—Elliptic.

*Base shape.*—Acuminate.

*Apex shape.*—Obtuse.

*Margin.*—Pinnatifid.

*Texture.*—Velvety.

*Pubescent.*—Slightly present.

*Leaf length.*—About 2.5 cm.

*Leaf width.*—About 1.5 cm.

*Color of upper surface.*—Mature leaf: Green group, RHS 137C. Immature leaf: Green group, RHS 137B.

*Color of lower surface.*—Mature leaf: Green group, RHS 138B. Immature leaf: Green group, RHS 138A.

*Venation color.*—Upper surface: Green group, RHS 137C. Lower surface: Green group, RHS 138C.

*Petiole.*—Length: About 10 mm. Diameter: About 1 mm. Color: Green group, RHS 138B.

Flower description:

*Natural flowering season.*—Spring throughout late fall.

*Lastingness of the bloom.*—Flowering of a single flower lasts for about 7 days.

*Quantity of flowers and buds per plant.*—About 200.

*Flower size.*—Diameter (spread): About 22 mm. Diameter at lobes: About 22 mm. Diameter of corolla tube: About 2 mm. Overall flower height: About 10 mm.

*Flower bud.*—Height: About 10 mm. Diameter: About 5 mm. Color: Red group, RHS 46A.

*Petals.*—Overall shape: Rounded and gameopetalous. Apex: Rounded. Base: Fused. Length: About 8 mm. Width: About 7 mm. Margin: Entire. Texture: Velvety. Color: Upper surface, when opening: Red group, RHS 53A. Upper surface, opened flower: Red group RHS 53B. Lower surface, when opening: Red group RHS 53B. Lower surface, opened flower: Red group RHS 53D.

*Corolla throat color.*—Yellow-Orange group, RHS 14B.

*Corolla center* (*where petals are fused*).—Yellow-Orange group, RHS 21A.

*Calyx.*—Appearance: Deeply 5 lobed.

*Sepals.*—Quantity: 5. Shape: Oblong. Apex: Obtuse. Base: Fused. Margin: Entire. Length: About 6 mm. Diameter: About 2 mm. Upper surface color: Green group, RHS 138B. Lower surface color: Green group, RHS 138B.

*Pedicel.*—Aspect: Slanted upward. Length: About 14 mm. Diameter: About 1 mm. Angle: About 45°. Color: Yellow-Green group, RHS 146B.

Reproductive organs:

*Stamen.*—Number: 4. Color: Yellow-Orange group, RHS 21C.

*Anthers.*—Color: Yellow-Orange group, RHS 21C. Shape and length: Cylinder, About 1 mm.

*Pollen.*—Amount: Moderate. Color: Yellow-Orange group, RHS 21C.

*Pistils.*—Quantity: 1. Length: About 6 mm.

*Stigma.*—Shape: Rounded. Color: Green group, RHS N164B.

*Ovary.*—Color: Green group, RHS 140D.

Seeds:

*Width.*—About 0.5 mm.

*Length.*—About 0.5 mm.

*Shape.*—Rounded.

*Texture.*—Rough.

*Color.*—Brown group, RHS 200A.

Fruit:

*Width.*—About 2 mm.

*Length.*—About 4 mm.

*Shape.*—Ellipsoid.

*Texture.*—Rough.

*Color.*—Greyed-orange group, RHS 165B.

Disease/pest resistance: No information is currently available.

Disease/pest susceptibility: Whiteflies; insecticidal soaps can cause foliage burn. Drench with fungicide registered for pythium at liner planting.

I claim:

1. A new and distinct *Jamesbrittenia* plant named 'DABRIT1', substantially as illustrated and described herein.

* * * * *